United States Patent
Uziel et al.

(10) Patent No.: US 9,835,563 B2
(45) Date of Patent: Dec. 5, 2017

(54) EVALUATION SYSTEM AND A METHOD FOR EVALUATING A SUBSTRATE

(71) Applicant: APPLIED MATERIALS ISRAEL LTD., Rehovot (IL)

(72) Inventors: Yoram Uziel, Misgav (IL); Ron Naftali, Shoham (IL); Ofer Adan, Rehovot (IL); Haim Feldman, Nof-Ayalon (IL); Ofer Shneyour, Hod-Hasharon (IL); Ron Bar-Or, Ramat-Gan (IL); Doron Korngut, Modiin (IL)

(73) Assignee: APPLIED MATERIALS ISRAEL LTD., Rehovot (IL)

( * ) Notice: Subject to any disclaimer, the term of this patent is extended or adjusted under 35 U.S.C. 154(b) by 78 days.

(21) Appl. No.: 14/946,693

(22) Filed: Nov. 19, 2015

(65) Prior Publication Data
US 2016/0077016 A1    Mar. 17, 2016

Related U.S. Application Data

(63) Continuation of application No. PCT/IB2014/061637, filed on May 22, 2014.
(Continued)

(51) Int. Cl.
*G01N 21/00* (2006.01)
*G01N 21/88* (2006.01)
(Continued)

(52) U.S. Cl.
CPC ........... *G01N 21/88* (2013.01); *G01Q 10/065* (2013.01); *G01Q 20/02* (2013.01); *G01Q 60/06* (2013.01); *G01Q 60/24* (2013.01); *G01Q 70/06* (2013.01)

(58) Field of Classification Search
CPC ........ G01N 21/88; G01Q 60/24; G01Q 20/02; B82Y 20/00
See application file for complete search history.

(56) References Cited

U.S. PATENT DOCUMENTS 5,317,141 A    5/1994  Thomas et al.
5,939,709 A *  8/1999  Ghislain ............... B82Y 20/00
                                                    250/216
(Continued)

FOREIGN PATENT DOCUMENTS

CN    105339799         2/2016
WO    2014188379 A1    11/2014

OTHER PUBLICATIONS

PCT/IB2014/061637, "International Search Report and Written Opinion", dated Sep. 16, 2014, 9 pages.
(Continued)

*Primary Examiner* — Jamil Ahmed
(74) *Attorney, Agent, or Firm* — Kilpatrick Townsend & Stockton LLP

(57) ABSTRACT

There may be provided an evaluation system that may include spatial sensors that include atomic force microscopes (AFMs) and a solid immersion lens. The AFMs are arranged to generate spatial relationship information that is indicative of a spatial relationship between the solid immersion lens and a substrate. The controller is arranged to receive the spatial relationship information and to send correction signals to the at least one location correction element for introducing a desired spatial relationship between the solid immersion lens and the substrate.

20 Claims, 10 Drawing Sheets

Related U.S. Application Data

(60) Provisional application No. 61/826,945, filed on May 23, 2013.

(51) Int. Cl.
*G01Q 10/06* (2010.01)
*G01Q 20/02* (2010.01)
*G01Q 60/06* (2010.01)
*G01Q 70/06* (2010.01)
*G01Q 60/24* (2010.01)

(56) References Cited

U.S. PATENT DOCUMENTS

| | | |
|---|---|---|
| 7,149,036 B2 | 12/2006 | Arata et al. |
| 7,221,502 B2 | 5/2007 | Terada et al. |
| 7,359,115 B2 | 4/2008 | Arata et al. |
| 7,414,800 B2 | 8/2008 | Isobe et al. |
| 7,480,051 B2 | 1/2009 | Frank et al. |
| 7,526,158 B2 | 4/2009 | Brown et al. |
| 7,692,138 B1 * | 4/2010 | Ray ............... B82Y 20/00 250/216 |
| 8,767,199 B2 | 7/2014 | Dozor et al. |
| 2011/0216312 A1 | 9/2011 | Matsumoto et al. |

OTHER PUBLICATIONS

"NanoLens (Solid Immersions Lens), "Resolution and light collection efficiency greatly improved by increasing numerical aperture (N.A.)"", Technical Note, www.hamamatsu.com.cn/UserFiles/DownFile/Related/e_nanolens.pdf, 2009, 2 pgs.

\* cited by examiner

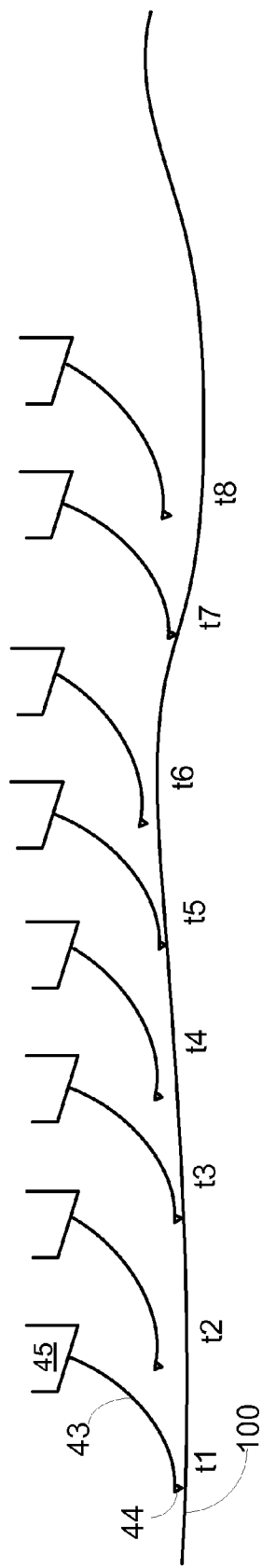

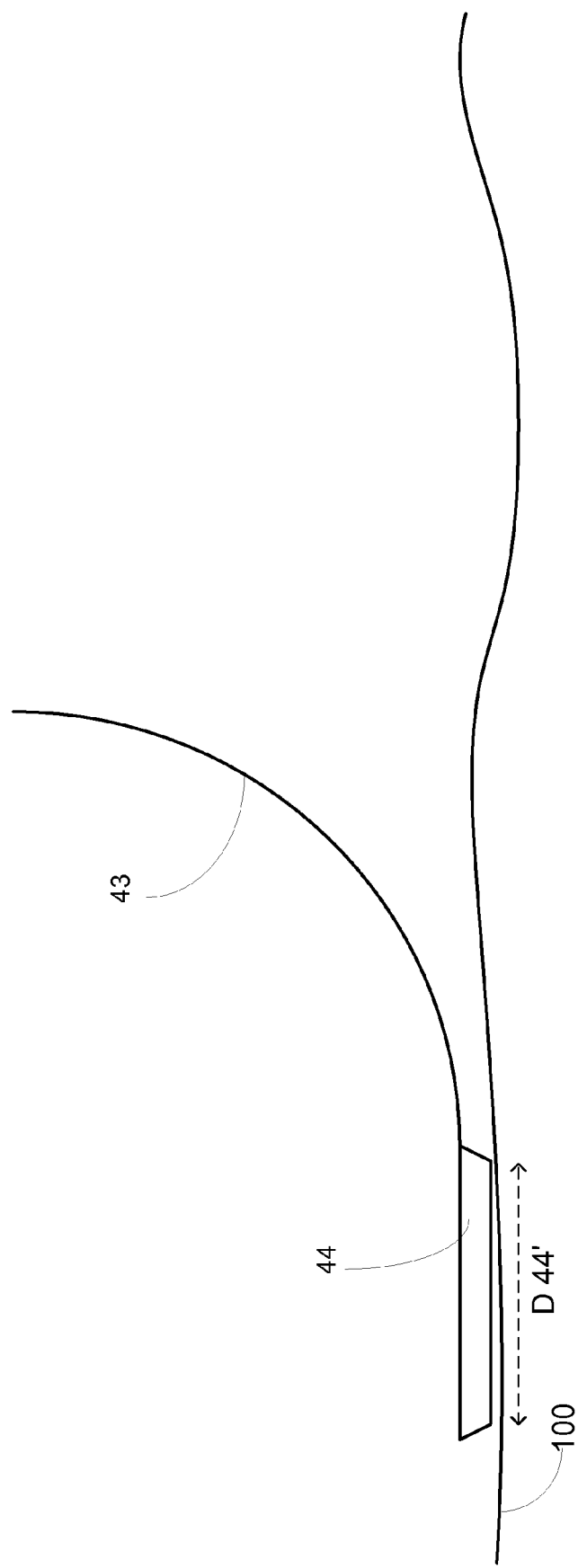

Evaluating a substrate. The evaluating may include scanning by a solid immersion lens a substrate while attempting to maintain a desired spatial relationship between the solid immersion lens and the substrate. 310

Generating by multiple spatial sensors (that include one or more AFMs) spatial relationship information that may be indicative of a spatial relationship between the solid immersion lens and the substrate. 312

Receiving by a controller the spatial relationship information and sending correction signals to at least one location correction element for attempting to introduce the desired spatial relationship between the solid immersion lens and the substrate. 314

Changing the spatial relationship between the solid immersion lens and the substrate by the at least one location correction element in response to the correction signals. 316

EVALUATION SYSTEM AND A METHOD FOR EVALUATING A SUBSTRATE

CROSS-REFERENCES TO RELATED APPLICATIONS

This application is a continuation of and claims priority to PCT/IB2014/061637, filed May 22, 2014; which claims the benefit of U.S. Provisional Patent Application No. 61/826,945, filed May 23, 2013. The disclosures of each of the PCT/IB2014/061637 and 61/826,945 applications are herein incorporated by reference in their entirety for all purposes.

BACKGROUND OF THE INVENTION

Evaluation systems are required to detect smaller and smaller defects. Additionally or alternatively, evaluation systems are required to measure or detect smaller and smaller structural elements. Today, extreme ultra violet evaluation systems and deep ultra violet evaluation systems are required to detect smaller defects and smaller structural elements.

Solid immersion lenses are used for imaging and evaluation of substrates, with improved resolution. This is described for example, in U.S. Pat. Nos. 7,526,158; 7,221,502, 7,149,036; 7,359,115; 7,414,800 and 7,480,051, in US Patent Applications Publication Serial Nos. 2011/0216312 and 2012/0092655, and in Technical Note/Nanolens (Solid Immersion Lens) by Hamamatsu (http://www.hamamatsu.com/resources/pdf/sys/e_nanolens.pdf).

There is a growing need to provide evaluation system of nanometric scale resolution.

BRIEF SUMMARY OF THE INVENTION

According to various embodiments of the invention there may be provided an evaluation system that may include: multiple spatial sensors; a solid immersion lens; a supporting structure; at least one location correction element; and a controller. The supporting structure is connected to the spatial sensors, to the solid immersion lens and to the at least one location correction element. Each spatial sensor is arranged to generate spatial relationship information that is indicative of a spatial relationship between the solid immersion lens and a substrate. The controller is arranged to receive the spatial relationship information and to send correction signals to the at least one location correction element for introducing a desired spatial relationship between the solid immersion lens and the substrate. Wherein the multiple spatial sensors include multiple atomic force microscopes (AFMs).

Each AFM may include a cantilever, a tip, a cantilever holder, a cantilever illuminator that may be arranged to illuminate a cantilever and a detector that may be arranged to sense light deflected from the cantilever.

The multiple AFMs may include at least three non-collinear AFMs.

The multiple AFMs may include at least four non-collinear AFMs.

Each AFM may include an oscillator for oscillating the cantilever.

The tip may exceed 10 nanometers.
The tip may exceed 50 nanometers.
The tip may exceed 100 nanometers.
The AFMs may be arranged to perform a coarse scanning of the substrate.

The AFMs may be arranged to scan the substrate without contacting the substrate.

The AFMs may be arranged to scan the substrate while contacting the substrate.

The evaluation system may include a calibration station for calibrating the multiple AFM modules.

The supporting structure may be arranged to place the solid immersion lens at a distance of less than 100 nanometers from the substrate.

The supporting structure may be arranged to place the solid immersion lens at a distance of less than 50 nanometers from the substrate.

The evaluation system may include location correction elements that are arranged to elevate at least one of the multiple spatial sensors in relation to the solid immersion lens.

The evaluation system may include a mechanical movement module arranged to introduce a movement between the supporting structure and the substrate.

The mechanical movement module may be arranged to introduce a movement of at least 50 millimeter per second between the supporting structure and the substrate.

At least one spatial sensor may be a capacitance sensor.

According to an embodiment of the invention there may be provided a method for evaluating a substrate, the method may include scanning by a solid immersion lens a substrate while attempting to maintain a desired spatial relationship between the solid immersion lens and the substrate; wherein the attempting to maintain the desired spatial relationship may include: generating by multiple spatial sensors spatial relationship information that is indicative of a spatial relationship between the solid immersion lens and the substrate; wherein the multiple spatial sensors may include multiple atomic force microscope (AFM); receiving by a controller the spatial relationship information and sending correction signals to at least one location correction element for attempting to introduce the desired spatial relationship between the solid immersion lens and the substrate; wherein the supporting structure is connected to the multiple spatial sensors, to the solid immersion lens and to the at least one location correction element.

Each AFM may include a cantilever, a tip, a cantilever holder, a cantilever illuminator that may be arranged to illuminate a cantilever and a detector that may be arranged to sense light deflected from the cantilever.

Any combinations of any of the components of any of the figures can be provided.

Any combination of any of the mentioned above systems can be provided.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof may best be understood by reference to the following detailed description when read with the accompanying drawings in which:

FIG. 3 illustrates cantilevers, tips and cantilever holders at different points of time while scanning a substrate according to an embodiment of the invention;

FIG. 4 illustrates a cantilever, a tip and a substrate according to an embodiment of the invention;

FIG. 6 illustrates a method according to an embodiment of the invention;

Figure 1:
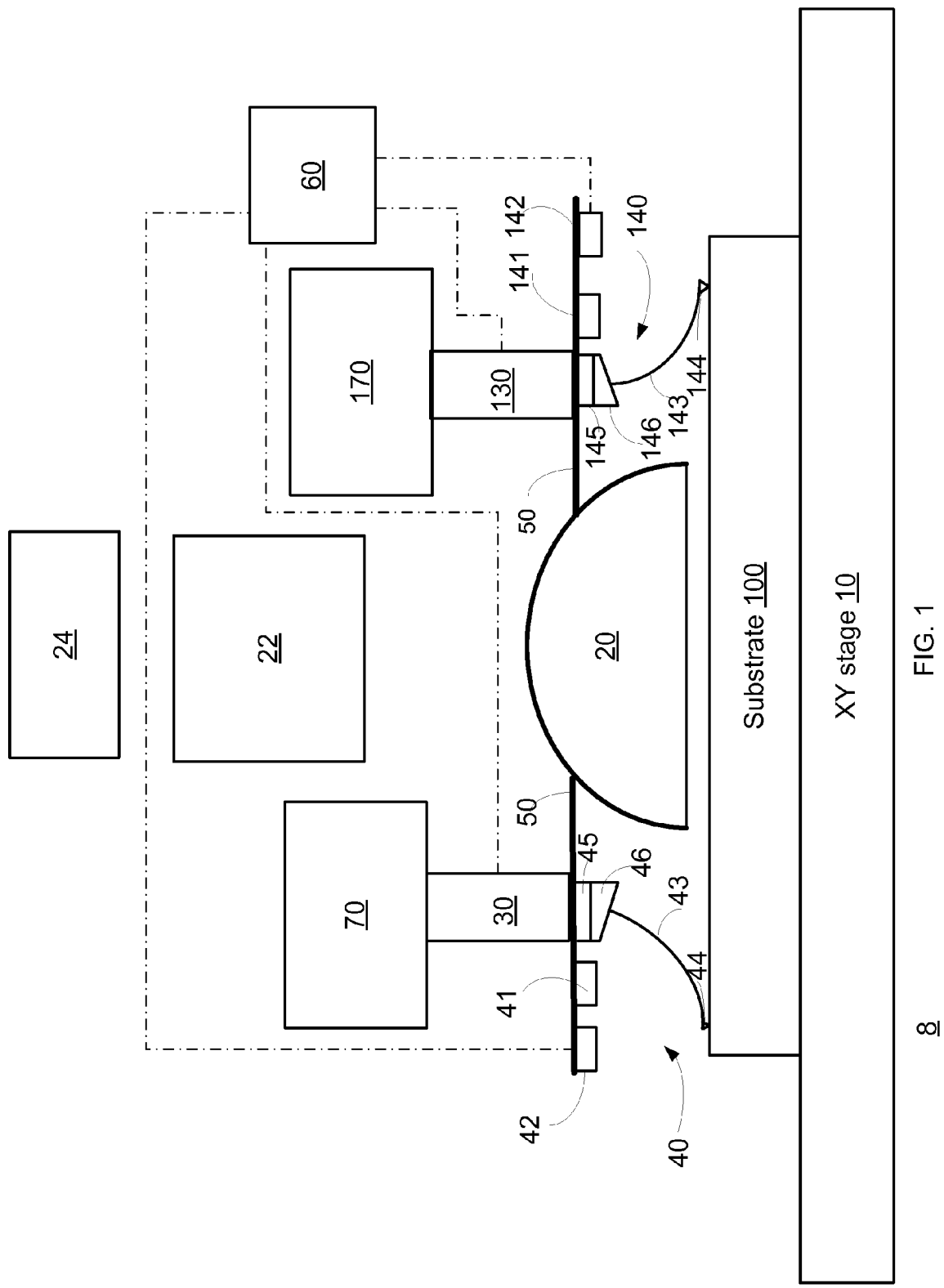
FIG. 1 illustrates an evaluation system according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

Because the illustrated embodiments of the present invention may, for the most part, be implemented using electronic components and modules known to those skilled in the art, details will not be explained in any greater extent than that considered necessary as illustrated above, for the understanding and appreciation of the underlying concepts of the present invention and in order not to obfuscate or distract from the teachings of the present invention.

The assignment of the same reference numbers to various components may indicate that these components are similar to each other.

There may be provide an evaluation system that includes a solid immersion lens that is maintained at a desired spatial relationship (or at an almost desired spatial relationship) with the substrate and thus allowing the solid immersion lens to operate in an optimal or near optimal manner.

According to an embodiment of the invention, the solid immersion lens can be maintained at substantially the desired spatial relationship by using atomic field microscopes (AFMs) that provide highly accurate spatial relationship information about the actual spatial relationship between the solid immersion lens and the substrate.

According to other embodiments of the invention, other techniques and components, or a combination of more than one technique, are used for providing highly accurate spatial relationship information about the actual spatial relationship between the solid immersion lens and the substrate.

An Atomic Force Microscope (AFM) is a very high-resolution type of scanning probe microscope with demonstrated resolution on the order of fractions of a nanometer, more than 1000 times better than the optical diffraction limit (www.wikipedia.org).

The AFM is one of the foremost tools for imaging, measuring, and manipulating matter at the nanoscale. Height information is gathered by scanning a surface with a mechanical probe (cantilever).

Piezoelectric elements that facilitate tiny but accurate and precise movements on (electronic) command enable the very precise scanning. In some variations, electric potentials can also be scanned using conducting cantilevers. In newer more advanced versions, currents can even be passed through the cantilever tip to probe the electrical conductivity or transport of the underlying surface, but this is much more challenging with very few research groups reporting consistent data.

An AFM includes a cantilever with a sharp tip (probe) at the cantilever end that is used to scan the specimen surface. The cantilever is typically made of silicon or silicon nitride with a tip radius of curvature on the order of nanometers. When the tip is brought into proximity of a substrate surface, forces between the tip and the substrate lead to a deflection of the cantilever according to Hooke's law.

Depending on the situation, forces that are measured by the AFM include mechanical contact force, van der Waals forces, capillary forces, chemical bonding, electrostatic forces, magnetic forces, solvation forces, etc. Along with force, additional quantities may simultaneously be measured through the use of specialized types of probe (see scanning thermal microscopy, scanning joule expansion microscopy, photothermal microspectroscopy, etc.).

Typically, the deflection of the cantilever is measured using a laser spot reflected from the top surface of the cantilever into an array of photodiodes. Other methods that are used include optical interferometry, capacitive sensing or piezoresistive AFM cantilevers. These cantilevers are fabricated with piezoresistive elements that act as a strain gauge. Using a Wheatstone bridge, strain in the AFM cantilever due to deflection can be measured.

The primary modes of operation for an AFM are static mode and dynamic mode. Obtaining tip-to substrate distance information in both static and dynamic modes is known in the art.

In static mode, the cantilever is "dragged" across the surface of the substrate and substrate's characteristics (e.g. the contours of the surface, height of features on the surface, and more) are measured directly using the deflection of the cantilever.

In the dynamic mode, the cantilever is externally oscillated at or close to the cantilever fundamental resonance frequency or a harmonic. The oscillation amplitude, phase and resonance frequency are modified by tip-substrate interaction forces. These changes in oscillation with respect to the external reference oscillation provide information about the substrate's characteristics. Thus, a tip-to substrate distance can be reflected by one or more of the oscillation amplitude, phase and resonance frequency. For example—the amplitude of the oscillation decreases as the tip gets closer to the substrate. Measuring the tip-to-substrate distance at each (x,y) data point allows the scanning software to construct a topographic image of the substrate surface.

Evaluation System

FIG. 1 illustrates an evaluation system 8 and substrate 100 according to an embodiment of the invention.

The evaluation system 8 may include one or more atomic force microscopes (AFMs). In the embodiment illustrated in FIG. 1, two AFMs 40 and 140 are shown, as well as solid immersion lens 20, supporting structure 50, controller 60, optics 22, light source and sensor module 24 and at least one location correction element (two location correction elements are shown in FIGS. 1-30 and 130). The location correction elements may be piezoelectric motors.

Each AFM (40, 140) includes a cantilever (43, 143), a tip (44, 144), a cantilever holder (46, 146), a cantilever illuminator (41, 141) that is arranged to illuminate the cantilever (43, 143) and a detector (42, 142) that is arranged to sense light deflected from the cantilever (43, 143).

FIG. 1 also shows the AFMs as including oscillators (45, 145) for oscillating the cantilevers (43, 143) during a dynamic mode. Oscillators (45,145) are illustrated as contacting cantilever holders (45, 145).

The supporting structure 50 is connected to the multiple AFMs 40 and 140, to the solid immersion lens 20 and to location correction elements 30 and 130.

The location correction elements 30 and 130 interface between the supporting structure 50 and fixed structural elements 70 and 170. The location of the supporting structure 50 in relation to the fixed structural elements 70 and 170 may change by the location correction elements 30 and 130, thereby change the spatial relationship between the solid immersion lens 20 and the substrate 100.

The AFMs 40 and 140 are arranged to generate spatial relationship information that is indicative of a spatial relationship between the solid immersion lens 20 and substrate 100.

According to an embodiment of the invention, the spatial information can define the distance between the solid immersion lens 20 and the substrate 100 at a single point or at multiple points.

Acquiring three or more distance measurements from three or more different locations may provide information about the orientation of the solid immersion lens 20 and the substrate 100.

According to another embodiment of the invention, the spatial information can define various tilts between the solid immersion lens 20 and the substrate 100. The tilts can be defined along non-parallel axes such as imaginary axes 11 and 12 of FIG. 2. The tilts can be computed along a scan axis of the inspection head (combination of the AFM and the solid immersion lens) and can be used to compensate for changes in the orientation and/or distance of the inspection head along the scan axis (such as imaginary axes 11 and 12) and maintain a desired spatial relationship between the substrate and the inspection head.

The number and location of the location correction elements (30 and 130) can correspond to the number and location of the AFMs (40, 140)—but this is not necessarily so. There may be more location correction elements than AFMs or less location correction elements than AFMs. The AFMs can be located at substantially the same locations as the location correction elements but this is not necessarily so.

Referring back to FIG. 1—the controller 60 is arranged to receive the spatial relationship information and to send correction signals to the at least one location correction element (30, 130) for introducing a desired spatial relationship between the solid immersion lens and the substrate. Each one of the location correction elements (30,130) can move the supporting structure 50 along one or more axes, perform a rotation and the like.

The number of AFMs may exceed two, three, four, five and even more. At least some of the AFMs may be arranged in a non-collinear manner.

Figure 2A:
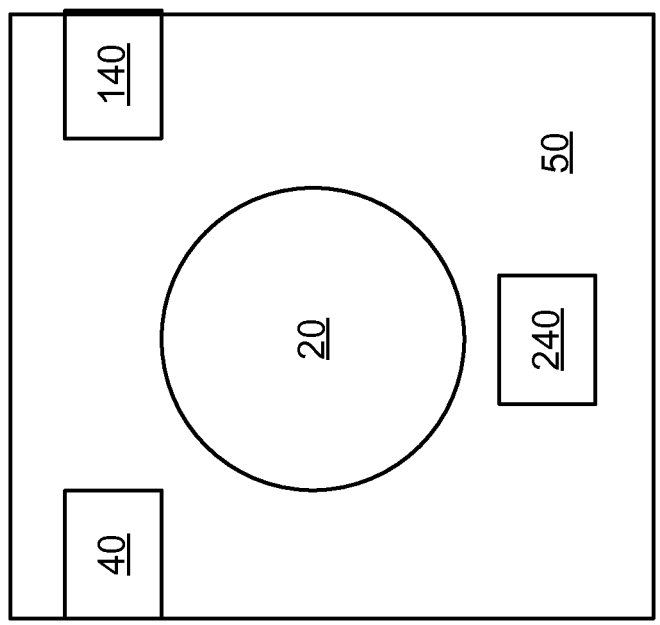
FIGS. 2A-2B illustrate inspection heads according to various embodiments of the invention.

FIG. 2A illustrates an inspection head 11A according to an embodiment of the invention that includes a solid immersion lens 20, supporting structure 50 and four AFMs 40, 140, 240 and 340.

Figure 2B:
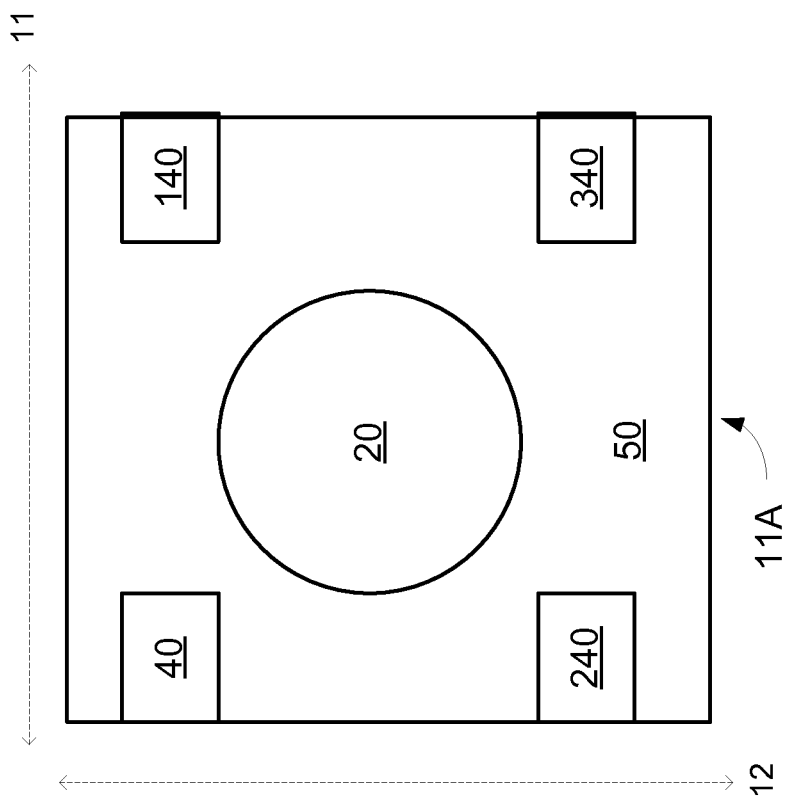

FIG. 2B illustrates an inspection head 11B according to an embodiment of the invention that includes three AFMs 40, 140 and 240, supporting structure 50 and solid immersion lens 20.

The AFMs of any evaluation system may be arranged in a symmetrical or asymmetrical manner in relation to the supporting structure 50 and/or in relation to the solid immersion lens 20.

FIG. 3 illustrates cantilever 43, tip 44 and cantilever holder 45 at different points of time (t1-t8) while scanning a substrate 100 according to an embodiment of the invention.

FIG. 3 illustrates an oscillation of the cantilevers while scanning the substrate 100 along a scan axis that is parallel to the plain of the page. FIG. 3 shows that at four point of time (t1, t3, t5, t7) that represent the lowest points of cantilever oscillation, the tip is very close to the substrate (may contact the substrate or may not contact the substrate) while in other points of time (t2, t4, t6, t8) that represent the highest points of cantilever oscillation, the tip is much distant than the substrate 100. At different points of time the cantilever senses different heights.

FIG. 4 illustrates a cantilever 43, a tip 44 and a substrate 100 according to an embodiment of the invention.

According to an embodiment of the invention, the tip 44 is relatively wide comparing to the curvatures of the substrate 100 and when the tip 44 scans the surface of the substrate 100 the tip 44 may (due to the size of the tip) virtually perform an averaging operation on the shape of the surface. The width (D 44') of tip 44 may be or may exceed 10, 20, 30, 40, 50, 60, 70, 80, 90 and 100 nanometers.

Figure 5:
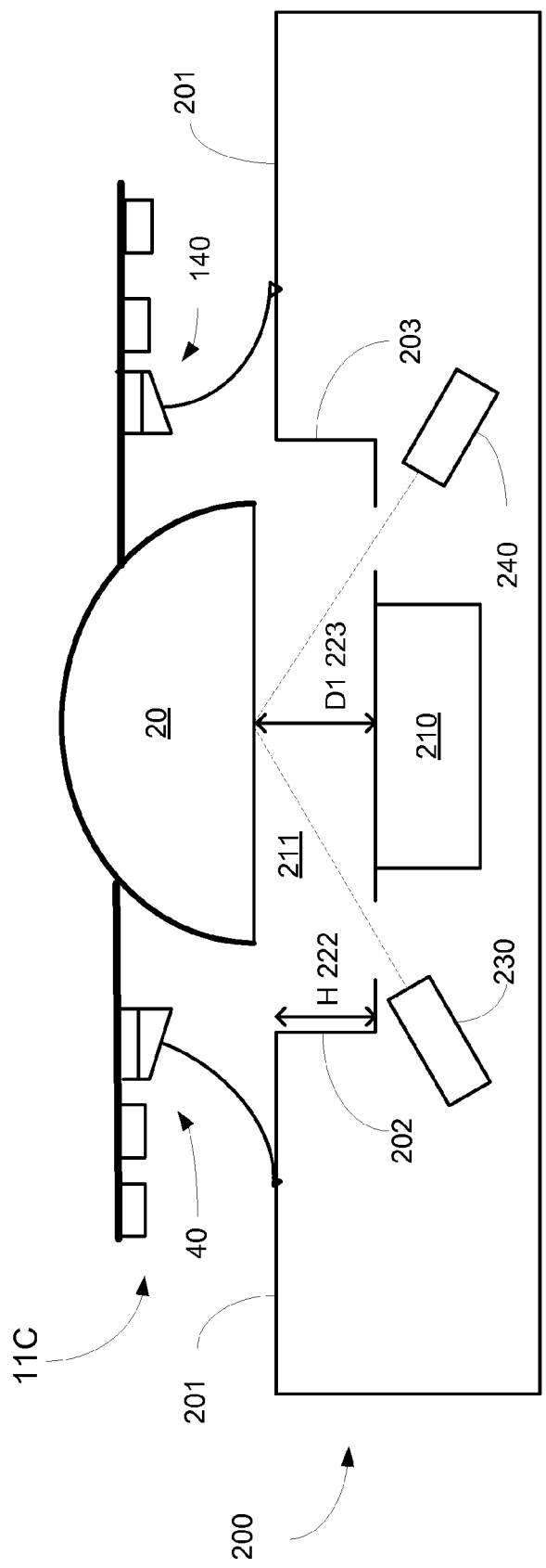
FIG. 5 illustrates a calibration station and an inspection head of the evaluation system according to an embodiment of the invention.

FIG. 5 illustrates a calibration station 200 and an inspection head 11C of the evaluation system according to an embodiment of the invention.

Calibration station 200 has a void 211 of a predetermined height H 222 and may have sidewalls 202 and 203 that end upper surface 201. The void is shaped and sized so that the tips of the cantilevers of the AFMs 40, 140 of the inspection head 11C contact the upper surface 201 while the solid immersion lens 20 is positioned above the void.

A proximity sensor 210 is positioned below the void 211 and can measure the distance Dl 223 between bottom of the void 211 and the solid immersion lens 20.

The AFMs 40, 140 provide each a distance reading and the values of the distance reading are used for determining the difference between Dl and H.

It is assumed that the proximity sensor is more accurate than the AFMs or at least of the same accuracy as the AFMs. By comparing the height measurements of the AFMs 40 AND 140 (measuring the difference between Dl and H), to the proximity readings (measuring Dl) of the proximity sensor 210, and given the height H 222 of the void 211 of the calibration station 200 there is provides a mapping between values of AFM readings and the distance (height) between the solid immersion lens 20 and an inspected surface of a substrate.

The calibration station 200 may be a part of an evaluation station or may be a separate station.

A relative angle between the solid immersion lens 20 and the void 211 may affect the measurements of the proximity sensor 210 and of AFMs. This relative angle may be measured. An example of an evaluation of the relative angle is illustrated in FIG. 5. Beam source 230 and sensor 240 are positioned below void 211 (or below the location of the solid immersion lens 20) and are capable of estimating the tilt (relative angle) of the solid immersion lens 20 by illuminating (by beam source 230) the solid immersion lens 20 by radiation at a non-normal angle of incidence and by detecting (by sensor 240) reflected radiation from the solid immersion lens 20.

FIG. 6 illustrates method 300 according to an embodiment of the invention.

Method 300 may include step 310 of evaluating a substrate. Step 310 may include scanning by a solid immersion lens a substrate while attempting to maintain a desired spatial relationship between the solid immersion lens and the substrate.

Step 310 and especially the attempting to maintain the desired spatial relationship may include:
1. Generating (312), by multiple spatial sensors (that may include one or more AFMs), spatial relationship information that may be indicative of a spatial relationship between the solid immersion lens and the substrate.
2. Receiving (314), by a controller, the spatial relationship information and sending correction signals to at least one location correction element for attempting to introduce the desired spatial relationship between the solid immersion lens and the substrate.
3. Changing (316) the spatial relationship between the solid immersion lens and the substrate, by the at least one location correction element, in response to the correction signals.

Step 310 may be executed by an evaluation system as described in FIG. 1.

Dual Stage System

Figure 7:
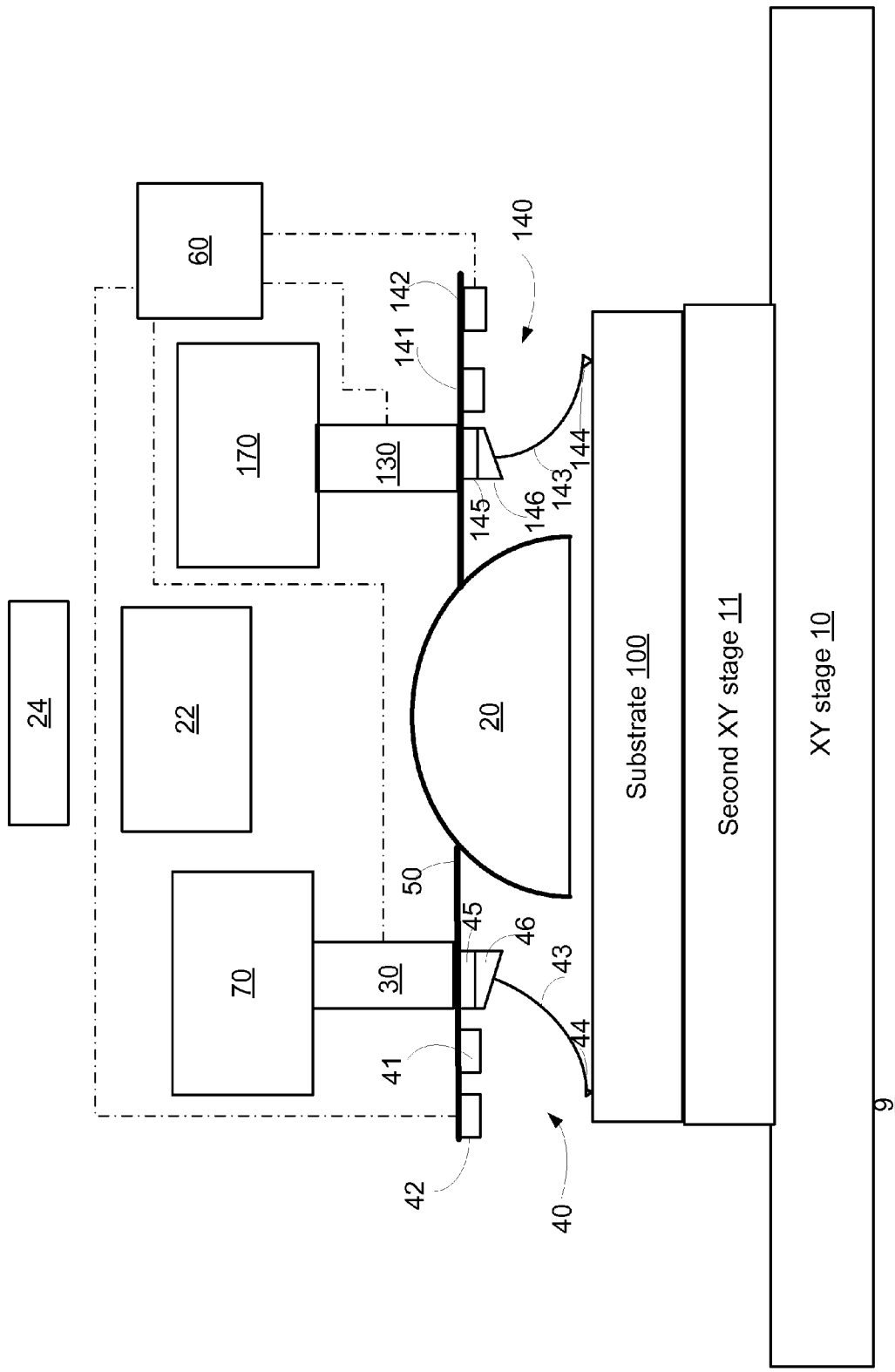
FIG. 7 illustrates an evaluation system according to an embodiment of the invention.

FIG. 7 illustrates an evaluation system 9 and substrate 100 according to an embodiment of the invention.

The evaluation system may include two mechanical stages, as illustrated in FIG. 7, in order to reduce expected jitter associated with the movement of the multiple AFMs, the solid immersion lens and the supporting structure (collectively referred to as near-object elements).

The evaluation system 9 of FIG. 7 differs from the evaluation system 8 of FIG. 1 by having two mechanical stages such as XY stage 10 and second XY stage 12 instead of a single XY stage.

According to various embodiments of the invention the near-object elements are moved by using XY stage 10 and second XY stage 12. XY stage 10 is heavier than the second XY stage 12 and supports second XY stage 12.

The XY stage 10 may follow a first scan pattern and does not stop (according to an embodiment of the invention) when moving along a scan line. Especially—the XY stage 10 does not stop when a suspected defect is imaged.

The movement along the first scan line can be of a constant velocity but this is not necessarily so and this movement can include accelerations and decelerations which are usually moderate in relation to accelerations and decelerations introduced by a second XY stage 12.

According to an embodiment of the invention, the second XY stage 12 may be smaller in size and weight comparing the first stage (e.g. "nano-stage" or "micro-stage"). The second XY stage 12 may move along a relatively small field of view (in relation to the movement of the XY stage 10) that may span along few millimeters or few centimeters. Thus, a more accurate and less jittered movement of the near-object elements can be provided.

Both XY stage 10 and second XY stage 12 may move the near-object elements within a XY plane. Both XY stage 10 and second XY stage 12 may also include a Z-stage for moving the near-object elements in the Z direction (not shown in FIG. 7).

The invention is not limited by the type of XY stage 10 and second XY stage 12. The second XY stage 12 may use magnetic levitation (maglev, or magnetic suspension) thereby supporting the object (which is suspended) with no support other than magnetic fields. Wikipedia indicates that magnetic pressure is used to counteract the effects of the gravitational and any other accelerations.

The second XY stage 12 may include a flexure bearing, may be a micro-stage that may include electrostatic comb-drive actuators such as illustrated in "Large range dual-axis micro-stage driven by electrostatic comb-drive actuators" by Mohammad Olfatnia, Leqing Cui, Pankaj Chopra and Shorya Awtar, IOP PUBLISHING JOURNAL OF MICROMECHANICS AND MICROENGINEERING page 23 (2013) or in U.S. Pat. No. 6,806,991 titled "Fully released MEMs XYZ flexure stage with integrated capacitive feedback" all being incorporated herein by reference.

The second XY stage 12 is expected to smooth the movement of the near-object elements.

Spatial Sensing Options

The invention is not limited by the kind of techniques and type of components which are used for sensing the relations of the solid immersion lens and the surface. The height (or other spatial relationships) of the solid immersion lens with respect to the surface can be monitored using spatial detectors that differ from AFMs and may be performed using a combination of AFMs and other sensors.

A first example of a spatial sensor that differs from an AFM is a capacitance sensor. The capacitance sensor may be responsive to (a) the spatial difference between the capacitance sensor and the substrate and (b) to additional factors such as the materials from which a sensed area of the substrate is made of (for example different readings may be expected when the capacitance sensor is above a conductor or above an insulator).

In order to provide a measurement that is height sensitive and is not sensitive (or at least not substantially sensitive) to other factors, a calibration process may be performed. For example, during the calibration process, the capacitance sensor may scan the substrate at a fixed spatial relationship. The fixed spatial relationship measurements are used as reference measurements that may be used for compensating for the additional factors that may impact the reading.

Figure 8:
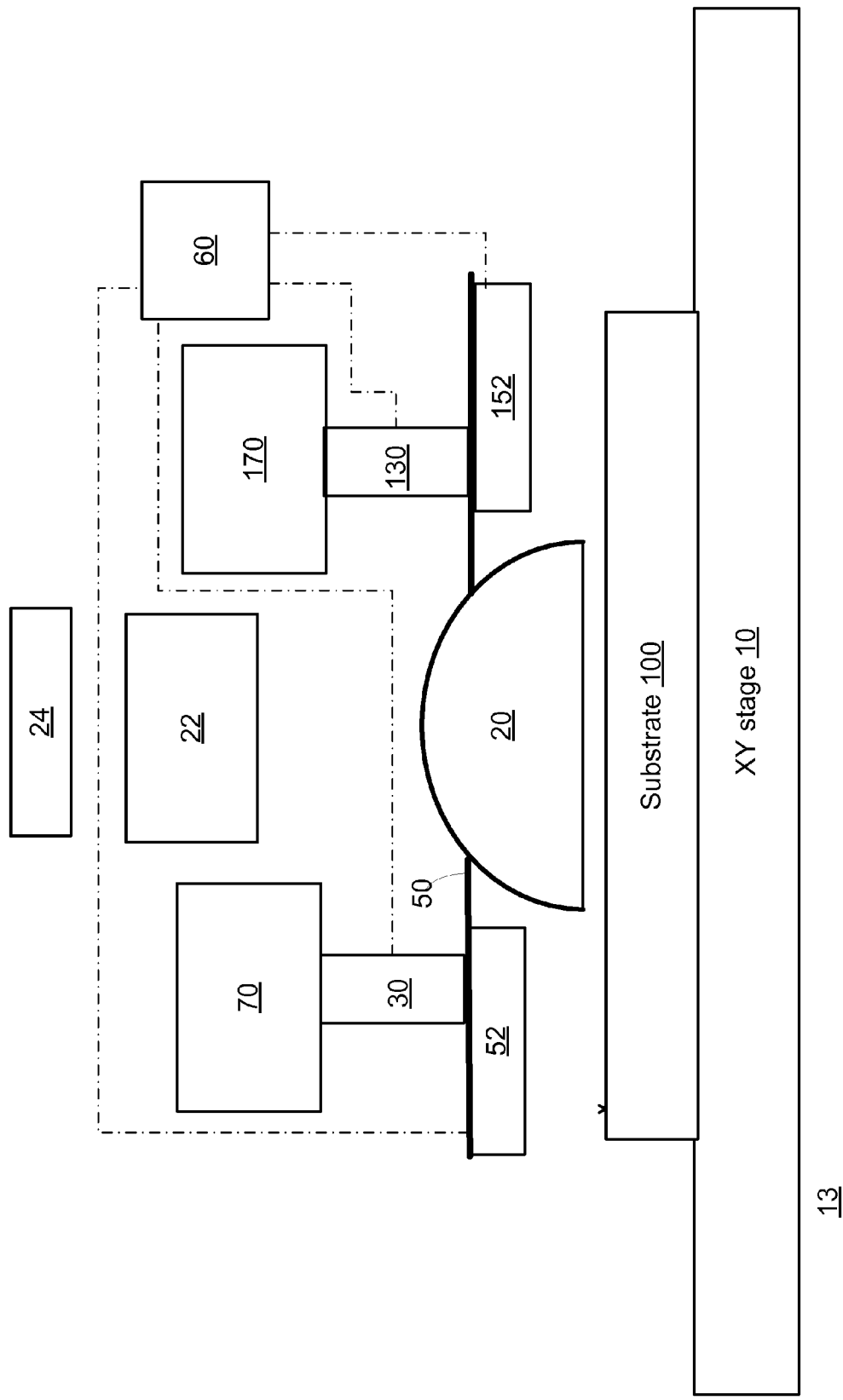
FIG. 8 illustrates an evaluation system according to an embodiment of the invention.

FIG. 8 illustrates an evaluation system 13 and substrate 100 according to an embodiment of the invention.

The evaluation system 13 of FIG. 8 differs from the evaluation system 8 of FIG. 1 by having spatial sensors 52 and 152 that differ from AFMs 40 and 140. Two such sensors 52 and 152 are illustrated in FIG. 8. However, the invention is not limited to two spatial sensors 52 and 152. Each one of the spatial sensors may be a capacitance sensor or another spatial sensor. Each spatial sensor may be a part of an auto-focus system.

The invention can be implemented by employing one or more AFMs and one or more capacitance sensor or another spatial sensor.

According to an embodiment of the invention, the spatial relation (e.g. height) between the solid immersion lens and the substrate is measured in a continuous manner while the solid immersion lens, which is carried by the inspection head, is scanning the substrate. According to other embodiments of the invention, the spatial relation sensors (AFMs or others) may be elevated when they are not expected to perform spatial measurements. The spatial sensors may be oscillated during scanning of the substrate.

Figure 9:
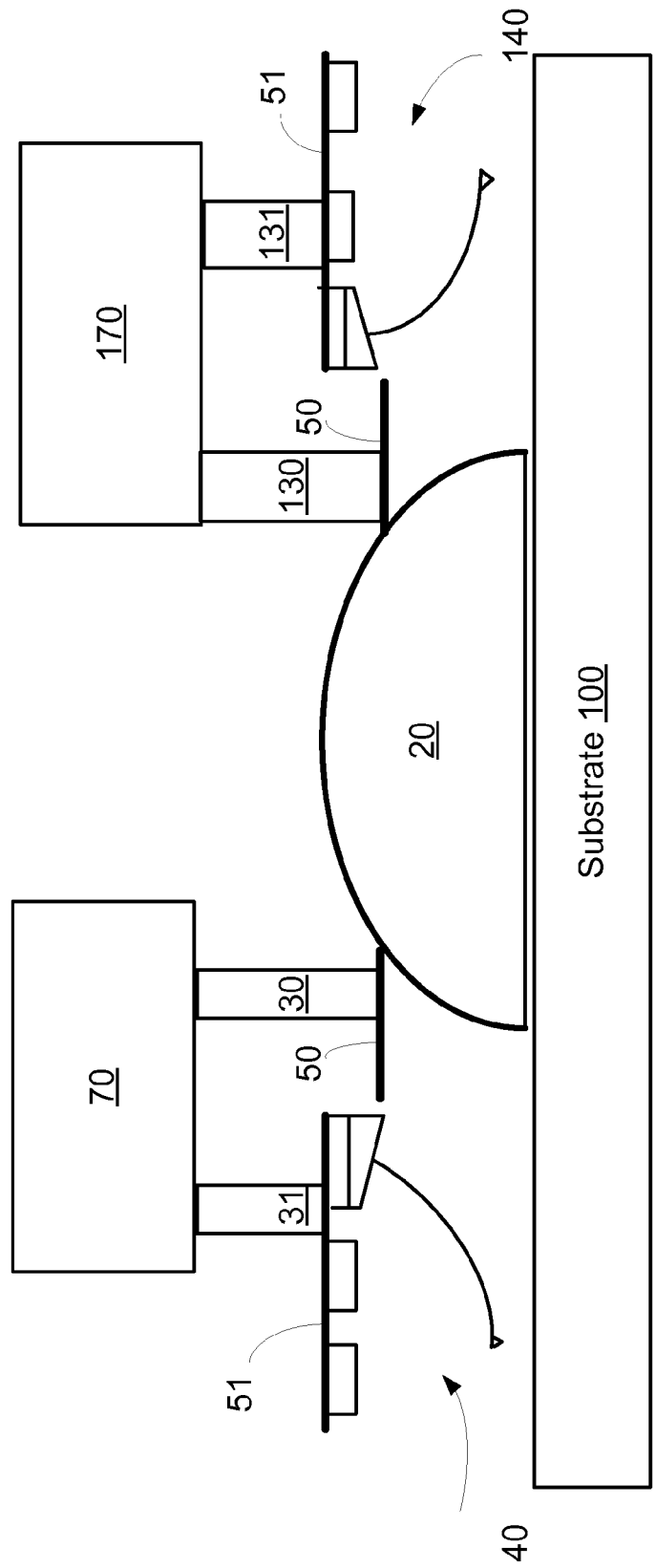
FIG. 9 illustrates an evaluation system according to an embodiment of the invention.

FIG. 9 illustrates substrate 100 and a portion 14 of an evaluation system according to an embodiment of the invention.

Portion 14 includes multiple AFMs such as AFMs 40 and 140, solid immersion lens 20, first supporting structure 50, second supporting structure 51, first location correction elements such as piezoelectric motors 30 and 130 and second location correction elements 31 and 131.

First location correction elements 30 and 130 are connected to first supporting structure 50 and interface between the first supporting structure 50 and fixed structural elements 70 and 170. The first location correction elements 30 and 130 may change the location of the first supporting structure 50 in relation to the fixed structural elements 70 and 170 and thereby change the spatial relationship between the solid immersion lens 20 and the substrate 100.

Second location correction elements 31 and 131 are connected to second supporting structures 51 and interface between the second supporting structures 51 and fixed structural elements 70 and 170. The second location correction elements 31 and 131 may change the location of the second supporting structures 51 in relation to the fixed structural elements 70 and 170 and thereby change the spatial relationship between the AFMs 40 and 140 and the substrate 100. Especially, the AFMs 40 and 140 may be elevated in relation to the substrate 100 such as not to contact the substrate 100 when not performing height measurements. For example—when moving from the vicinity of one defect to another.

Each AFM out of AFMs 40 and 140 can move independently from the other.

Figure 10:
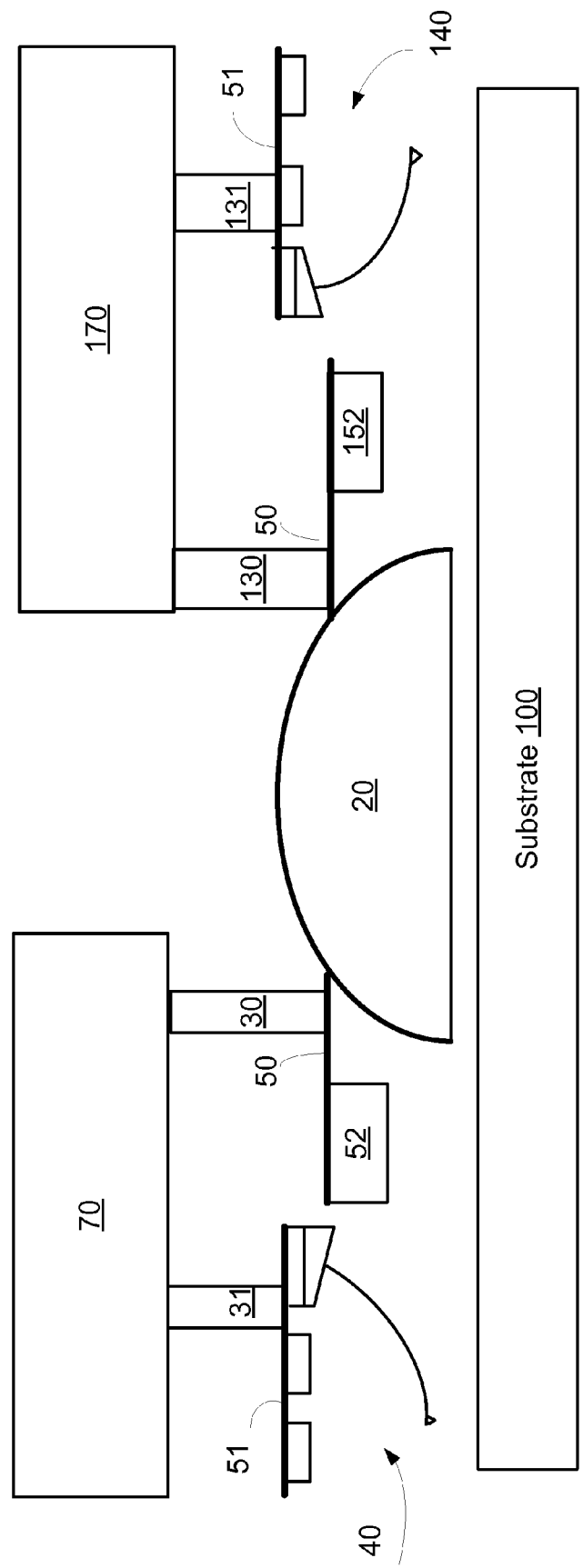
FIG. 10 illustrates an evaluation system according to an embodiment of the invention.

FIG. 10 illustrates substrate 100 and a portion 15 of an evaluation system according to an embodiment of the invention.

Portion 15 of FIG. 10 differs from portion 14 of FIG. 9 by including AFMs 40 and 140 and additional spatial sensors 52 and 152 that differ from AFMs 40 and 140.

The additional spatial sensors 52 and 152 may be used for height estimation while the AFMs are elevated—but this is not necessarily so. For example the AFMs 40 and 140 may be lowered when reaching a vicinity of a suspected defect or when reaching a new area to be scanned.

The height measurements may be sensed without using a dedicated height sensor but by processing optical signals reflected or scattered from the substrate.

In the foregoing specification, the invention has been described with reference to specific examples of embodiments of the invention. It will, however, be evident that various modifications and changes may be made therein without departing from the broader spirit and scope of the invention as set forth in the appended claims.

Furthermore, the terms "assert" or "set" and "negate" (or "deassert" or "clear") are used herein when referring to the rendering of a signal, status bit, or similar apparatus into its logically true or logically false state, respectively. If the logically true state is a logic level one, the logically false state is a logic level zero. And if the logically true state is a logic level zero, the logically false state is a logic level one.

Those skilled in the art will recognize that the boundaries between logic blocks are merely illustrative and that alternative embodiments may merge logic blocks or module elements or impose an alternate decomposition of functionality upon various logic blocks or module elements. Thus, it is to be understood that the architectures depicted herein are merely exemplary, and that in fact many other architectures can be implemented which achieve the same functionality.

Any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

Furthermore, those skilled in the art will recognize that boundaries between the above described operations merely illustrative. The multiple operations may be combined into a single operation, a single operation may be distributed in additional operations and operations may be executed at least partially overlapping in time. Moreover, alternative embodiments may include multiple instances of a particular operation, and the order of operations may be altered in various other embodiments.

Also for example, in one embodiment, the illustrated examples may be implemented as circuitry located on a single integrated circuit or within a same device. Alternatively, the examples may be implemented as any number of separate integrated circuits or separate devices interconnected with each other in a suitable manner.

Also for example, the examples, or portions thereof, may implemented as soft or code representations of physical circuitry or of logical representations convertible into physical circuitry, such as in a hardware description language of any appropriate type.

However, other modifications, variations and alternatives are also possible. The specifications and drawings are, accordingly, to be regarded in an illustrative rather than in a restrictive sense.

In the claims, any reference signs placed between parentheses shall not be construed as limiting the claim. The word 'comprising' does not exclude the presence of other elements or steps then those listed in a claim. Furthermore, the terms "a" or "an," as used herein, are defined as one or more than one. Also, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles. Unless stated otherwise, terms such as "first" and "second" are used to arbitrarily distinguish between the elements such terms describe. Thus, these terms are not necessarily intended to indicate temporal or other prioritization of such elements. The mere fact that certain measures are recited in mutually different claims does not indicate that a combination of these measures cannot be used to advantage.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An evaluation system, comprising:
   a solid immersion lens;
   a plurality of spatial sensors, each spatial sensor in the plurality of spatial sensors being arranged to generate spatial relationship information indicative of a spatial relationship between a respective location of a plurality of locations on the solid immersion lens and a substrate, wherein the plurality of spatial sensors comprises multiple atomic force microscopes (AFMs);
   at least one location correction element;
   a controller arranged to receive the spatial relationship information and to send correction signals to the at least one location correction element for introducing a desired spatial relationship between the plurality of locations on the solid immersion lens and the substrate; and
   a supporting structure coupled to the spatial sensors, the solid immersion lens and the at least one location correction element.

2. The evaluation system according to claim 1 wherein each AFM comprises a cantilever, a tip, a cantilever holder, a cantilever illuminator that is arranged to illuminate the cantilever and a detector that is arranged to sense light deflected from the cantilever.

3. The evaluation system according to claim 1 wherein the multiple AFMs comprise at least three non-collinear AFMs.

4. The evaluation system according to claim 1 wherein the multiple AFMs comprise at least four non-collinear AFMs.

5. The evaluation system according to claim 1 wherein each AFM comprises an oscillator for oscillating a cantilever.

6. The evaluation system according to claim 1 wherein each AFM comprises a tip that exceeds 10 nanometers.

7. The evaluation system according to claim 1 wherein each AFM comprises a tip that exceeds 50 nanometers.

8. The evaluation system according to claim 1 wherein each AFM comprises a tip that exceeds 100 nanometers.

9. The evaluation system according to claim 1 wherein the AFMs are arranged to perform a coarse scanning of the substrate.

10. The evaluation system according to claim 1 wherein the AFMs are arranged to scan the substrate without contacting the substrate.

11. The evaluation system according to claim 1 wherein the AFMs are arranged to scan the substrate while contacting the substrate.

12. The evaluation system according to claim 1 further comprising a calibration station for calibrating the multiple AFM.

13. The evaluation system according to claim 1 wherein the supporting structure is arranged to place the solid immersion lens at a distance of less than 100 nanometers from the substrate.

14. The evaluation system according to claim 1 wherein the supporting structure is arranged to place the solid immersion lens at a distance of less than 50 nanometers from the substrate.

15. The evaluation system according to claim 1 comprising location correction elements that are arranged to elevate at least one of the plurality of spatial sensors in relation to the solid immersion lens.

16. The evaluation system according to claim 1 further comprising a mechanical movement module arranged to introduce a movement between the supporting structure and the substrate.

17. The evaluation system according to claim 16 wherein the mechanical movement module is arranged to introduce a movement of at least 50 millimeter per second between the supporting structure and the substrate.

18. The evaluation system according to claim 1 wherein at least one spatial sensor is a capacitance sensor.

19. A method for evaluating a substrate, the method comprising:
   scanning by a solid immersion lens a substrate while attempting to maintain a desired spatial relationship between a plurality of locations on the solid immersion lens and the substrate by:
      generating, by a plurality of spatial sensors, spatial relationship information that is indicative of a spatial relationship between the plurality of locations on the solid immersion lens and the substrate, the plurality of spatial sensors comprising multiple atomic force microscopes (AFMs); and
      receiving, by a controller, the spatial relationship information and sending correction signals to at least one location correction element for attempting to introduce the desired spatial relationship between the plurality of locations on the solid immersion lens and the substrate;
   wherein a supporting structure is connected to the plurality of spatial sensors, to the solid immersion lens and to the at least one location correction element.

20. The method according to claim 19 wherein each AFM comprises a cantilever, a tip, a cantilever holder, a cantilever illuminator that is arranged to illuminate the cantilever and a detector that is arranged to sense light deflected from the cantilever.

* * * * *